United States Patent [19]

Vlasich

[11] Patent Number: 5,048,727

[45] Date of Patent: Sep. 17, 1991

[54] PREASSEMBLED UNIT DOSE DISPENSER HAVING A COMPRESSIBLE CONTAINER AND A TUBE PREFILLED WITH A UNIT DOSE OF OPTHALMIC GEL.

[75] Inventor: Richard J. Vlasich, Fort Worth, Tex.

[73] Assignee: Alcon Laboratories, Inc., Forth Worth, Tex.

[21] Appl. No.: 522,393

[22] Filed: Apr. 30, 1990

Related U.S. Application Data

[63] Continuation of Ser. No. 667,625, Nov. 2, 1984, abandoned.

[51] Int. Cl.⁵ .............................................. B65D 37/00
[52] U.S. Cl. ................................... 222/209; 222/215; 222/394; 604/295; 401/185
[58] Field of Search ............... 222/206, 209, 632, 633, 222/215, 394; 604/294–296, 299; 401/183–187

[56] References Cited

U.S. PATENT DOCUMENTS

| | | | |
|---|---|---|---|
| 1,546,940 | 7/1925 | Pennington | 222/209 X |
| 2,332,798 | 10/1943 | Hunn | 222/209 X |
| 2,800,253 | 7/1957 | Henderson | 222/209 |
| 3,128,920 | 4/1964 | Volckeniuh et al. | 604/295 X |
| 4,299,258 | 11/1981 | Brite | 401/185 X |
| 4,331,264 | 5/1982 | Staar | . |
| 4,338,936 | 7/1982 | Nelson | 604/295 |
| 4,398,909 | 8/1983 | Portnoff | 604/295 |
| 4,416,397 | 11/1983 | Brown | . |

Primary Examiner—Michael S. Huppert
Assistant Examiner—Kenneth R. DeRosa
Attorney, Agent, or Firm—James A. Arno; Gregg C. Brown; Robert L. Price

[57] ABSTRACT

A unit dose dispenser for dispensing a composition includes a compressible, air filled container in communication with an open end of a tube filled with the composition. The opposite end of the tube through which the composition is dispensed is sealed with a removable closure cap to maintain sterility of the composition prior to use. By removing the cap and applying external pressure to compress the container, air is forced to enter the tube and eject, by displacement, composition from the tube. To completely eject the predetermined dosage that completely fills the tube, the volume of air or other gaseous propellant within the compressible container is greater than the volume of the unit dose.

3 Claims, 1 Drawing Sheet

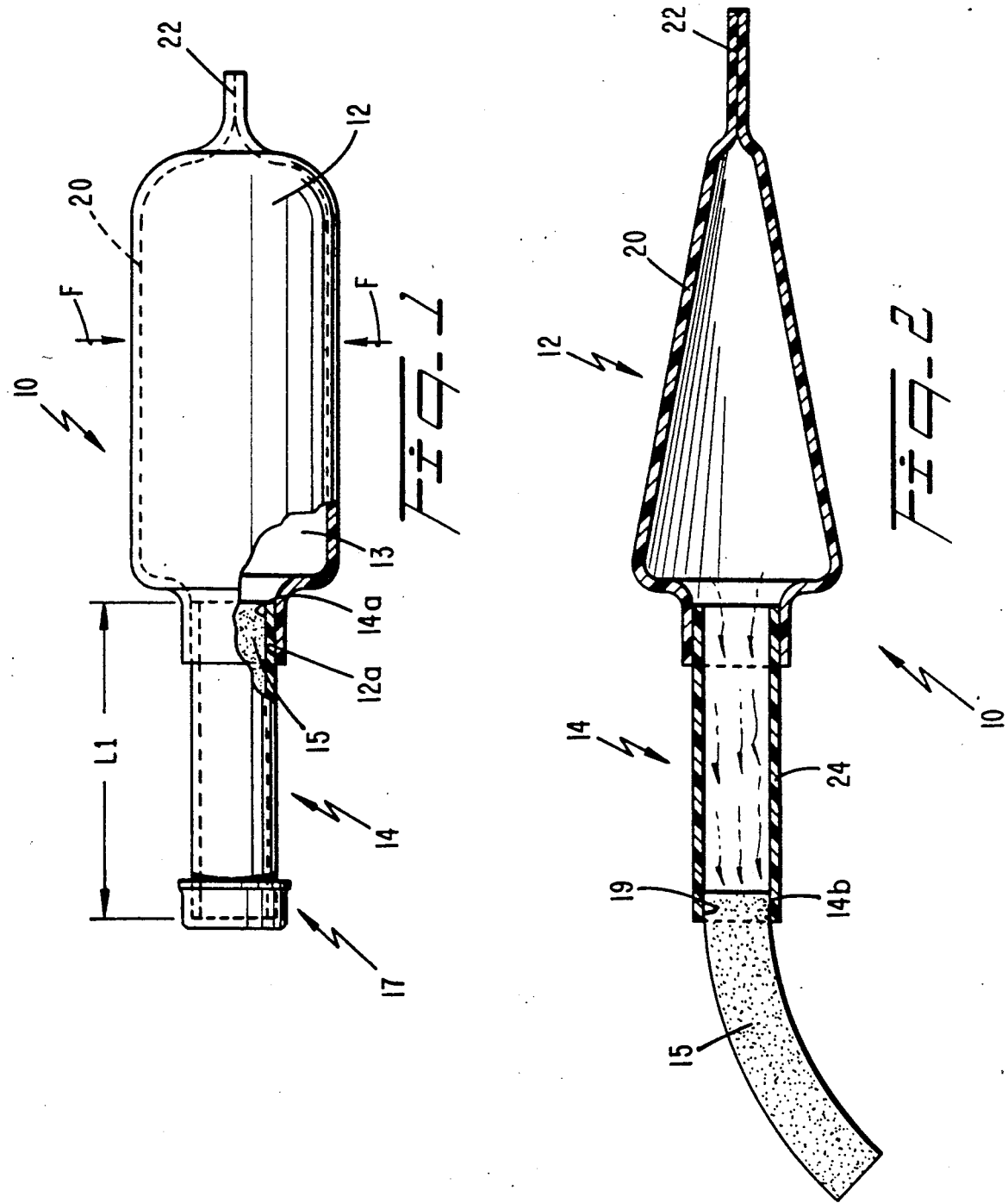

PREASSEMBLED UNIT DOSE DISPENSER HAVING A COMPRESSIBLE CONTAINER AND A TUBE PREFILLED WITH A UNIT DOSE OF OPTHALMIC GEL.

This application is a continuation of application Ser. No. 06/667,625 filed Nov. 2,1984 now abandoned.

TECHNICAL FIELD

The present invention relates generally to product dispensers and, more particularly, to a discardable dispenser used for dispensing a single unit dose of a gel-like composition.

BACKGROUND ART

Single dose dispensers for dispensing various type of products are disclosed, for example, in U.S. Pat. No. 4,331,264 to Staar, wherein a dispenser package is formed of two foil sections joined together to provide a compressible container filled with a flowable material. The container wall includes a rupture site separating the flowable material from a chamber provided with an outlet opening. When sufficient external pressure is applied against the container wall, the flowable material bursts the rupture site and flows into the chamber to escape through the outlet opening. A blocking wall formed within the chamber downstream from the rupture site provides throttling action so that material escapes at a constant flow rate and flow strength.

The aforesaid prior art dispenser is generally effective for dispensing small amounts or unit doses of a flowable material at a constant rate of discharge, independent of pressure applied to burst the rupture site. However, since pressure is applied directly to the compressible container wall containing the flowable material, there may be a tendency for residual amounts of material to remain in the container, for example, as a film remaining between opposing walls of the container as these walls are pressed into intimate contact with each other. Thus, the aforesaid prior art arrangement may be ineffective for dispensing single doses of a medicinal preparation, wherein it is often desirable and sometimes critical to assure that the entire predetermined dosage is discharged from the dispenser.

It is accordingly an object of the present invention to provide a unit dose dispenser capable of precisely discharging an entire predetermined dosage of a composition by preventing residual quantities or films of the composition from remaining in the dispenser.

Another problem associated with the aforesaid prior art dispenser is that the use of two hands may be necessary to provide sufficient pressure to burst the rupture site for dispensing composition. This may be particularly true for elderly or infirm individuals (e.g., arthritic persons) who cannot assert the necessary pressure with one hand to dispense the composition.

Another object of the present invention is to provide a unit dose dispenser capable of easy and reliable single handed operation by requiring application of only a slight amount of pressure against a dispenser side wall for dispensing composition.

Yet a further drawback of the prior art dispenser discussed above is that the outlet opening is formed flush and in the middle of one side of the joined foil sections. The width of the opening is small in relation to the effective length of the side edge. Thus, corner portions of the side edge tend to prevent accurate positioning or contact of the outlet opening with respect to certain areas on which composition is to be directly dispensed (e.g., the cul-de-sac of the human eye in situations where the composition to be dispensed is Pilocarpine).

Yet a further object is to to provide a unit dose dispenser having an applicator tip that can be easily positioned to dispense composition directly onto a desired area.

Still a further object is to provide a dispenser wherein the applicator tip cooperates with the remainder of the dispensing structure to assure that residual quantities of composition do not remain in the tip.

DISCLOSURE OF INVENTION

A unit dose dispenser for precisely dispensing a predetermined product dose, in accordance with the present invention, comprises first means having a first chamber for containing a propellant. The first chamber is formed with a side wall establishing the interior volumetric region thereof and an outlet opening through which the propellant can pass. A means is provided for decreasing the size of the volumetric region in response to external pressure applied against the side wall of the first chamber. A second means has a second chamber for containing the product. The second chamber includes a discharge opening and is connected to the first chamber so that in response to external pressure acting on the side wall of the first chamber, the propellant will pass from the first chamber to the second chamber to eject the product from the second chamber via gradual displacement therefrom.

In a preferred embodiment of the invention, the dispenser includes a compressible container filled with a gaseous medium as the propellant. The predetermined product dose is contained within a tube having one end attached to the outlet of the compressible container and an opposite end establishing the discharge opening. The discharge opening is preferably sealed with a removable closure cap to maintain sterility of the product prior to use.

The tube is preferably in open communications with the gaseous propellant in the compressible container, but may be separated from the gaseous propellant by means of a plastic plug barrier film, foil, or other suitable barrier means. Separation of the tube from the gaseous propellant may be necessary when the product contained in the tube is a liquid. The tube is preferably formed of a material that is sufficiently rigid to prevent the product stored therein from entering the compressible container should external pressure be inadvertently applied against the tubular side wall. In normal usage, after removing the cap, external pressure applied against the compressible container side wall causes the propellant to enter the tube to eject, by displacement, product contained within the tube.

The unit dose dispenser of the invention is preferably used to dispense gel-like compositions, such as ophthalmic gels, wherein the high viscosity of the composition substantially filling the dispensing tube provides excellent adhesion characteristics between the composition strip and interior cylindrical side wall of the tube to prevent the composition from entering the air filled compressible container.

In accordance with a further aspect of the present invention, a method of dispensing a single predetermined dosage of a gel-like composition directly onto a desired area of the human body is disclosed. The method comprises the steps of removing the closure cap to expose the discharge opening of the dispensing tube. The discharge opening is then positioned, via manipulation of the elongate dispenser tube to overlie or contact the desired area. The entire predetermined dosage is then discharged through the opening by application of external pressure to progressively collapse the compressible gas-filled chamber and cause the volume of propellant therein that is greater than the volume of the product to gradually enter the dispenser and eject, by displacement, the dosage from the dispenser.

Still other objects and advantages of the present invention will become readily apparent to those skilled in this art from the following detailed description, wherein I have shown only the preferred embodiment of the invention, simply by way of illustration of the best mode contemplated by me for carrying out my invention. As will be realized, the invention is capable of modifications in various aspects, all without departing from the invention. Accordingly, the drawings and description are to be regarded as illustrative in nature, and not as restrictive.

BRIEF DESCRIPTION OF THE DRAWING

FIG. 1 is a partly side and elevational view of a single dose product dispenser constructed in accordance with the present invention; and FIG. 2 is a sectional view of the dispenser shown in FIG. 1 in a collapsed state to dispense a unit dose of product contained within the dispenser.

BEST MODE FOR CARRYING OUT THE INVENTION

Referring to FIG. 1, a single unit dose dispenser 10 in accordance with the present invention comprises a compressible container 12 preferably filled with a gas propellant 13, such as air, and a product dispensing and storage tube 14 filled with a predetermined dose of a composition 15 to be dispensed. Tube 14 is sealingly connected at one open end 14a thereof to an outlet opening 12a of container 12 to provide open communication between composition 15 and the propellant. By removing a closure cap 17 to uncover a discharge opening 19 formed in the forward end 14b of tube 14, and by applying external pressure in the direction of arrows F to container 12, the gas is forced to flow under pressure into the tube. As it does so under continued application of external pressure, composition 15 is displaced from tube 14 through discharge opening 19 as a continuous strip of finite length L1 until the entire dose is dispensed.

Compressible container 12 includes a cylindrical side wall 20 preferably formed of a thermoplastic material such as polyethylene, polypropylene, polyvinyl chloride, copolymers and the like. Rear end portions of side wall 20 may be sealed together as by gluing, heat sealing or the like to obtain an air tight seal 22 while forward end portions may be heat sealed and pressed to establish outlet opening 12a.

The product storage and dispensing tube 14 has a cylindrical side wall 24 that may also be formed of a thermoplastic material. However, whereas container side wall 20 is sufficiently flexible to permit it to bow inwardly upon application of external force F (see FIG. 2) the tube side wall 24 is preferably of sufficient rigidity to resist the tendency to bow upon application of finger pressure. Composition 15 is thus prevented from being inadvertently squeezed into the interior volumetric gas filled region of container 12. Further, since composition 15 may be gel-like and therefore highly viscous, friction between the composition and the inner surface of the tube side wall 24 also tends to prevent the composition from entering container 12.

The air or other gaseous propellant contained within container 12 is preferably under atmospheric pressure. Thus, initial filling of dispenser 10 with composition 15 is easy since only suitable means (not shown) are necessary to inject a predetermined strip length L1 of composition into the storage tube 14. Thereafter, removable cap 17 is fitted, e.g., threaded, snap-fitted, friction-fitted, etc. to the forward end of the tube 14, to seal the discharge opening 19 to maintain the sterility of composition 15 until use is desired. Prior to use, cap 17 is removed. By applying external force F to the exterior side wall surface of container 12, air is forced to flow into tube 14 to displace composition 15 from the tube through discharge opening 19.

By containing composition 15 in a tube located downstream from container 12 in open communication with propellant stored therein, only slight finger pressure F is necessary to discharge composition from the tube. This is because it is unnecessary to apply a greater amount of pressure to burst a rupture site as disclosed in the prior art arrangement discussed above. Further, once cap 17 is removed, the user can easily position discharge opening 19 of tube 14 in close proximity to an area on which composition is to be discharged, accomplished by grasping container 12 with the fingers of one hand to guide the tube towards the discharge area. If desired, the fingers of the user's other hand may position the tube to facilitate further accurate positioning of discharge opening 19 with respect to the discharge area (e.g., the cul-de-sac of the eye).

The length and constant inner diameter of tube 14 determines the predetermined amount of composition 15 that can be dispensed from dispenser 10. Furthermore, by forming container 12 so that the volume of the interior volumetric region therein is greater than the volume in the dispensing tube, a sufficient quantity of air propellant is provided to assure that all of composition 15 is discharged through opening 19 via proportional displacement of air entering the tube under contained application of finger pressure F.

In this disclosure, there is shown and described only the preferred embodiment of the invention, but, as aforementioned, it is to be understood that the invention is capable of changes or modifications within the scope of the inventive concept as expressed herein.

I claim:

1. A preassembled, disposable, ophthalmic gel dispensing device, comprising:
   (a) a predetermined unit dosage of said ophthalmic gel;
   (b) a compressible container containing a gaseous propellant; and
   (c) a tube prefilled for containing said predetermined dose of gel, said tube having a discharge opening through which said predetermined gel dose is dispensed upon application of external pressure to the compressible container, causing the propellant to enter the tube and eject, by displacement, the gel from said tube, wherein said tube is substantially entirely prefilled with said unit dosage of gel which is contained only in the tube, said tube having one end permanently and directly fixed to an outlet formed directly in a side wall of said compressible container and an opposite end establishing said discharge opening, wherein said tube has a tubular side wall formed of a material that is sufficiently rigid to prevent the product stored therein from entering the compressible container when external finger pressure is applied to the tubular side wall, the volume of said tube as defined between opposite ends thereof being less than the volume of said compressible container so that substantially entirely all prefilled product in said tube is expelled in a single dosage by propellant; and a closure cap for sealing the discharge opening to protect the sterility of the prefilled product.

2. The device of claim 1, wherein said propellant is air.

3. The device of claim 1, wherein said compressible container includes a side wall formed of a flexible material, one end of said container side wall being closed by sealing together portions of said side wall, side wall portions forming the other end of the container establishing an opening receiving, in sealing contact, an end of said tubular side wall.

* * * * *

UNITED STATES PATENT AND TRADEMARK OFFICE
CERTIFICATE OF CORRECTION

PATENT NO. : 5,048,727

DATED : September 17, 1991

INVENTOR(S) : Vlasich

It is certified that error appears in the above-identified patent and that said Letters Patent is hereby corrected as shown below:

IN THE TITLE PAGE:

The word "OPTHALMIC" in the Title should be corrected to read --OPHTHALMIC--; and At column 1, the word "OPTHALMIC" in the Title should be corrected to read --OPHTHALMIC--.

Signed and Sealed this

Sixteenth Day of March, 1993

Attest:

STEPHEN G. KUNIN

*Attesting Officer*  *Acting Commissioner of Patents and Trademarks*